United States Patent
Wood et al.

(10) Patent No.: US 6,786,102 B2
(45) Date of Patent: *Sep. 7, 2004

(54) ULTRASOUND SPEED MEASUREMENT OF TEMPERATURE AND PRESSURE

(75) Inventors: Robert P. Wood, San Carlos, CA (US); Serge Plotkin, Belmont, CA (US); Jacob Harel, San Francisco, CA (US); Alfred Samson Hou, Sunnyvale, CA (US)

(73) Assignee: Luidia Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/435,859

(22) Filed: May 12, 2003

(65) Prior Publication Data

US 2003/0196476 A1 Oct. 23, 2003

Related U.S. Application Data

(63) Continuation of application No. 09/574,567, filed on May 17, 2000, now Pat. No. 6,571,643, which is a continuation-in-part of application No. 09/134,315, filed on Aug. 13, 1998, now Pat. No. 6,118,205.

(51) Int. Cl.$^7$ ................................................. G01F 1/66
(52) U.S. Cl. .................................................. 73/861.27
(58) Field of Search ..................... 73/896–598, 861.18, 73/861.25, 861.27, 861.28, 861.29, 861.31, 602, 624–625, 628, 632

(56) References Cited

U.S. PATENT DOCUMENTS

| | | |
|---|---|---|
| 3,432,691 A | 3/1969 | Shoh |
| 3,622,899 A | 11/1971 | Elsenburg |
| 3,689,781 A | 9/1972 | Kawada |
| 3,691,410 A | 9/1972 | Kawada |
| 3,694,713 A | 9/1972 | Duren et al. |
| 3,708,701 A | 1/1973 | Kawada |
| 3,819,961 A | 6/1974 | Bourgeois et al. |
| 3,824,447 A | 7/1974 | Kuwabara |
| 3,900,800 A | 8/1975 | Maltz |
| 3,975,650 A | 8/1976 | Payne |
| 4,053,821 A | 10/1977 | Hose, Jr. et al. |
| 4,054,806 A | 10/1977 | Moriki et al. |
| 4,070,589 A | 1/1978 | Martinkovic |
| 4,112,756 A | 9/1978 | MacLennan et al. |
| 4,262,545 A | 4/1981 | Lamarche et al. |
| 4,625,137 A | 11/1986 | Tomono |
| 4,963,703 A | 10/1990 | Phillips et al. |
| 5,073,878 A | 12/1991 | Gilchrist |
| 5,437,194 A | 8/1995 | Lynnworth |
| 6,571,643 B1 * | 6/2003 | Wood et al. .............. 73/861.27 |

FOREIGN PATENT DOCUMENTS

| | | |
|---|---|---|
| DE | 031 50 011 A1 | 6/1983 |
| DE | 196 17 961 A1 | 11/1997 |

* cited by examiner

Primary Examiner—Helen Kwok
(74) Attorney, Agent, or Firm—Dov Rosenfeld Inventek

(57) ABSTRACT

Methods and apparatus for using ultrasound to measure speed and acceleration in fluids is provided. Three exemplary embodiments are disclosed. The first exemplary embodiment measures fluid velocity, such as, for example, wind, under standard atmospheric pressure-temperature. The second exemplary embodiment measures gas velocity, such as, for example, wind, affected by and automatically calibrates for pressure-temperature. The third exemplary embodiment measures gas density, such as, for example, density altitude. Applications of the invention include wind direction and speed calculation in agriculture, aviation, hydraulics, and other industries. One of the advantages provided by the invention is there are no moving parts in making such measurements.

18 Claims, 2 Drawing Sheets

ULTRASOUND SPEED MEASUREMENT OF TEMPERATURE AND PRESSURE

REFERENCE TO RELATED APPLICATIONS

This application is a continuation of U.S. application Ser. No. 09/574,567, filed May 17, 2000, now U.S. Pat. No. 6,571,643, which is a continuation-in-part of U.S. application Ser. No. 09/134,315, filed Aug. 13, 1998, now U.S. Pat. No. 6,118,205.

FIELD OF THE INVENTION

The invention relates to measurement of speed and acceleration of fluids, in particular with regard to ultrasound technology.

BACKGROUND

The speed of sound in air along a line or path between any two points may be determined by measuring the time taken for the sound to travel between the two points. With the air moving from one point to the other, sound traveling in the same direction is speeded up, while sound traveling in the other direction is slowed down. Where the actual wind has a speed W in a direction which is at an angle $\theta$ to the sound speed line, then the wind component along that line is W cos $\theta$, and the wind component along a line that is perpendicular to the sound speed line is W sin $\theta$. In such a case, the sound speed S along the line is $S_o$+W cos $\theta$, where $S_o$ is the sound speed in still air. If the distance over which the sound speed is being measured is D, then the time T taken is D/S. Thus, T=D/($S_o$+W cos $\theta$).

Heard U.S. Pat. No. 4,336,606 ("Heard) discloses methods and apparatus for detecting and measuring a wind gradient at a location by comparing the wind speed in the same direction at two or more heights at the location. The comparison based upon a comparison of the speed of sound in a direction and at specific heights, a difference in the apparent speeds indicating the presence of wind gradient. The disclosure involves: beaming a regular sound wave train between a transmitter/receiver pair positioned and like orientated at each of two or more heights at the location; noting each transceiver pair's received sound wave train phase, and comparing it with its transmitted phase, so as to deduce the wind-caused phase change; and using these deduced phase changes to calculate the actual wind speeds, and thus the relative changes of wind speed with height, in the selected direction. Heard's apparatus, however, has the transmitter/receiver pairs positioned at too great a distance (approximately 200 feet) for the measurement to be effective and accurate. In addition, applying the teachings to an airplane landing situation is not practical as the noise level of an incoming plane is too large and will interfere with the accurate and timely measurements of the ultrasound transmissions.

Gill U.S. Pat. No. 5,163,331 ("Gill") discloses a fluid speed measurement device that includes a pair of ultrasonic transducers spaced in a measuring chamber. A transmitter and receiver system is controlled by a microprocessor which generates pulses which periodically invert and these are switched by switches that allow alternate direction of transmission. Reception and detection of signals is effected by particular blocks. Time calculation is determined by a counter and results are used to calculate flow speed or volume using a microprocessor. A speed increase in the measurement region is effected using a venturi device. The device disclosed in Gill, however, is a closed device. In a closed configuration, the speed of a gas is higher than the speed of the same gas in an open configuration. The disclosed system therefore is not required to be sufficiently sensitive to detect signals in such a fluid wherein the speed is not so high, as in, for example, the atmosphere.

Herrmann et al. U.S. Pat. No. 5,804,739 ("Herrmann") discloses a "method of determining the time point ($t_o$) of the start of a high frequency oscillation packet triggered as a result of a corresponding external excitation which is extremely tolerant relative to systematic disturbances from various sources that consists of determining the times at at least two points of the envelope curve of the oscillation packet with respect to an arbitrary zero time point. Of these two points one is a characteristic point of the envelope curve and the other has an amplitude equal to a predetermined fraction of the amplitude at the characteristic envelope curve point. It is preferable that during ". . . calculation the angle between the directions of the ultrasonic pulse packets and the flow direction of the medium, . . . differs significantly from 90 degree, is particularly taken into account." Hermann does not, however, disclose nor suggest automatic calibration for pressure-temperature, nor portability, no that the size of the measuring device be of a relative small size.

It would be advantageous to provide a fluid speed measurement apparatus along with a process that takes digital measurements.

It would be advantageous to provide a fluid speed measurement apparatus along with a process that uses a protective, ventilated material, such as, for example, a lightweight plastic, to allow for automatic calibration to pressure-temperature.

It would be advantageous to provide a fluid speed measurement apparatus along with a process that is small enough and portable to be used at an airplane runway for measuring wind velocity and direction, yet placed far enough away from the runway so that loud airplane noises cannot interfere with the measurement apparatus and process.

It would be advantageous to provide a fluid speed measurement apparatus along with a process that has no moving parts, such as, for example, a ventilator or moving flap used in detecting fluid speed.

SUMMARY

Methods and apparatus for using ultrasound technology to measure speed and acceleration in fluids are provided. Three exemplary embodiments are disclosed. The first exemplary embodiment measures fluid velocity, such as, for example, wind, under standard atmospheric pressure-temperature. The second exemplary embodiment measures fluid velocity, such as, for example, wind, affected by and automatically calibrates for pressure and temperature. The third exemplary embodiment measures gas or air density, such as, for example, density altitude. Applications of the invention include wind direction and speed calculation in agriculture, aviation, hydraulics, and other industries.

BRIEF DESCRIPTION OF THE DRAWINGS

The above-mentioned objects and features of the present invention can be more clearly understood from the following detailed description considered in conjunction with the following drawings, in which the same reference numerals denote the same elements throughout, and in which.

DETAILED DESCRIPTION

Methods and apparatus for using ultrasound technology to measure speed and acceleration in fluids are provided. Three preferred embodiments are disclosed. The first exemplary embodiment measures fluid velocity, such as, for example, wind, under standard atmospheric pressure and temperature. The second exemplary embodiment measures fluid velocity, such as, for example, wind, affected by and automatically calibrates for pressure and temperature. The third exemplary embodiment measures fluid density, such as, for example, density altitude. Applications of the invention include wind direction and speed calculation in agriculture, aviation, hydraulics, and other industries.

Figure 1:
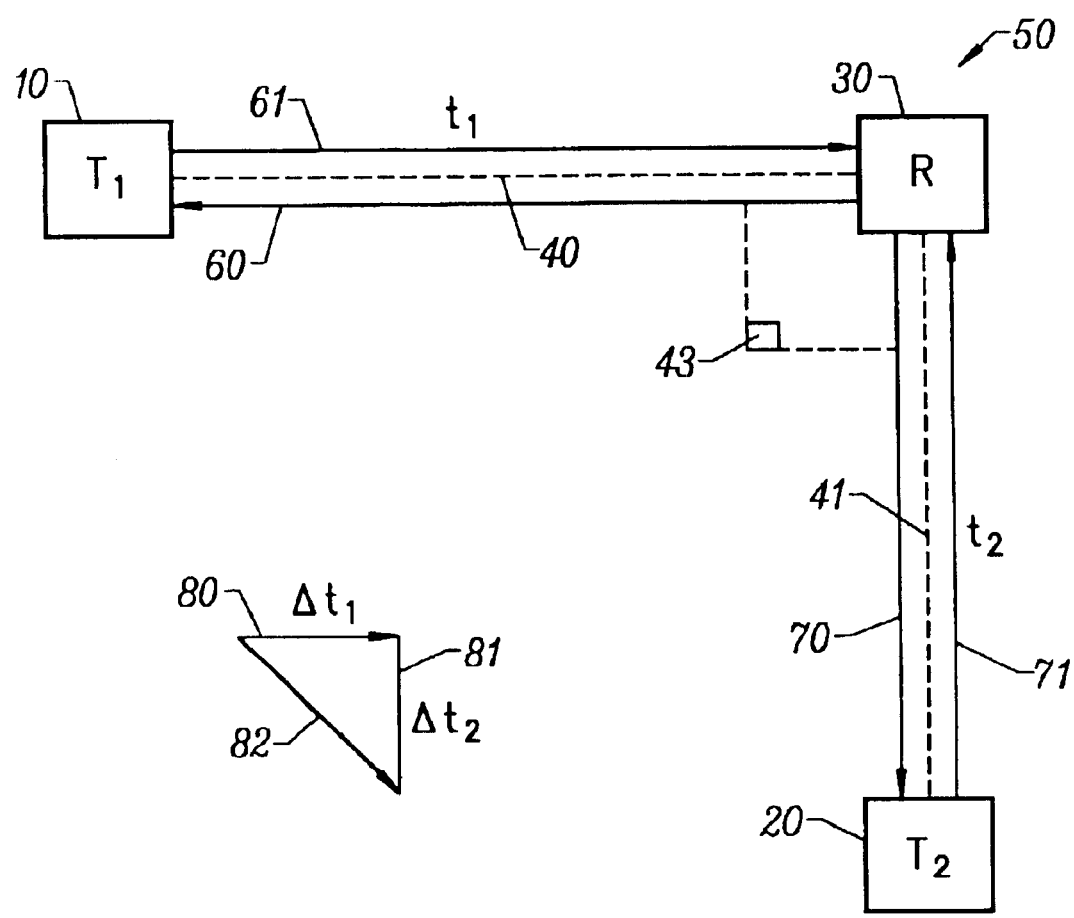
FIG. 1 is a diagram of the first preferred embodiment, according to the invention.

FIG. 1 is a diagram of a first exemplary embodiment of an apparatus for calculating a wind velocity vector in standard atmospheric pressure. A first transmitter element 10, $T_1$, is adapted to transmit ultrasonic pulses. A second transmitter element 20, $T_2$, is also adapted to transmit ultrasonic pulses. A receiver element 30 is adapted to receive ultrasonic pulses. The first transmitter 10 is positioned a relatively short distance of about 2 feet from the receiver 30. The second transmitter 20 is also positioned a short distance 41 of about 2 feet from the receiver 30 and positioned at a 90 degree angle 43 from the first transmitter 10. The first transmitter 10, the second transmitter 20, and the receiver 30 are placed in an open configuration 50.

The time transit vector 60 of a generic ultrasonic pulse from the receiver 30 to the first transmitter 10 in standard atmospheric pressure with no wind is a predetermined entity. Similarly, the time transit vector 70 of a generic ultrasonic pulse from the receiver 30 to the second transmitter 20 in standard atmospheric pressure with no wind is a predetermined entity. A time transit vector 61, $t_1$, from the first transmitter 10 to the receiver 30 is calculated. A second time transit vector 71, $t_2$, from the second transmitter 20 to the receiver 30 is calculated.

A first transit time differential vector 80 is determined by taking the difference between the first transit time vector 61 and the predetermined transit time vector 60 of the generic ultrasonic pulse in standard atmospheric pressure. Similarly, a second transit time differential vector 81 is determined by taking the difference between the second transit time vector 71 and the predetermined transit time vector 70 of the generic ultrasonic pulse in standard atmospheric pressure. A resultant fluid velocity vector 82 is determined by combining the first transit time differential vector 80 and the second transit time differential vector 81.

Figure 2:
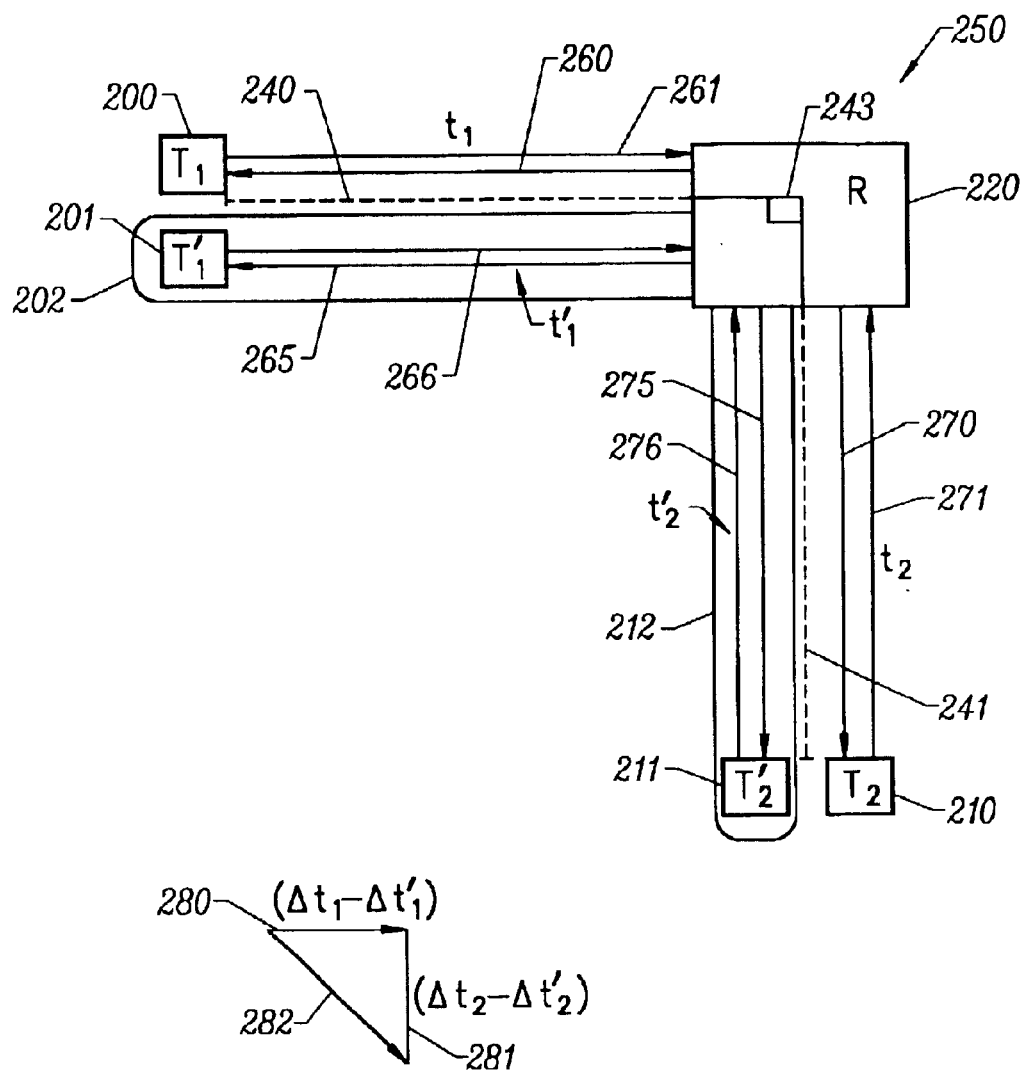
FIG. 2 is a diagram of the second preferred embodiment, according to the invention.

FIG. 2 is a diagram of a second exemplary embodiment of an apparatus for calculating an automatically calibrated fluid velocity vector in external pressure-temperature. A first transmitter element 200 is adapted to transmit ultrasonic pulses, and a first transmitter primed element 201 is adapted to transmit ultrasonic pulses. The first transmitter element 200 is placed in an open configuration 250 and the first transmitter primed element 201 is placed in a ventilated tube 202. The first transmitter primed element 201 is positioned along a vertical axis of the first transmitter element 200.

A second transmitter element 210 is adapted to transmit ultrasonic pulses, and a second transmitter primed element 211 is adapted to transmit ultrasonic pulses. The second transmitter element 210 is placed in the open configuration 250 and the second transmitter primed element 211 is placed in a second ventilated tube 212. The second transmitter primed element 211 is positioned along a second axis of the second transmitter element 210, wherein the second axis is perpendicular to the first axis.

A receiver element 220 is adapted to receive ultrasonic pulses from the first transmitter 200, the first transmitter primed 201, the second transmitter 210, and the second transmitter primed 211. The first transmitter 200 and the first transmitter primed 201 are each positioned a first short distance 240 from the receiver 220. The second transmitter 210 and the second transmitter primed 211 are each positioned a second short distance 241 from the receiver 220, and are each positioned at a 90 degree angle from 243 the first transmitter 200 and the first transmitter primed 201.

A time transit vector 260 of an ultrasonic pulse from the receiver 220 to the first transmitter 200 in the open configuration 250 is a predetermined entity. A time transit vector 265 of an ultrasonic pulse from the receiver 220 to the first transmitter primed 201 in the ventilated tube is a predetermined entity. Similarly, a time transit vector 270 of an ultrasonic pulse from the receiver 220 to the second transmitter 210 in the open configuration 250 is a predetermined entity. A time transit vector 275 of an ultrasonic pulse from the receiver 220 to the second transmitter primed 211 in the ventilated tube is a predetermined entity.

An ultrasonic time transit vector 261, $t_1$, from the first transmitter 200 to the receiver 220 is calculated. An ultrasonic time transit vector 266, $t_1$, from the first transmitter primed 201 to the receiver 220 is calculated. Similarly, a second ultrasonic time transit vector 271, $t_2$, from the second transmitter 210 to the receiver 220 is calculated. A second ultrasonic time transit primed vector 276, $t_2$, from the second transmitter primed 211 to the receiver 220 is calculated.

A first transit time differential vector, $\Delta t_1$, by taking the difference between the calculated first transit time vector 261 and the predetermined time transit vector 260 is calculated. A first transit time differential vector primed, $\Delta t_1$, by taking the difference between the calculated first transit time vector primed 266 and the predetermined time transit vector primed 265 is calculated. Similarly, a second transit time differential vector, $\Delta t_2$, by taking the difference between the calculated second transit time vector 271 and the predetermined time transit vector 270 is calculated. A second transit time differential vector primed, $\Delta t'_2$, by taking the difference between the calculated second transit time vector primed 276 and the predetermined time transit vector primed 275 is calculated.

A first automatically calibrated fluid velocity component vector 280 is determined by taking the difference between the first transit time differential vector, $\Delta t_1$, and the first transit time differential vector primed, $\Delta t'_1$. Similarly, a second automatically calibrated fluid velocity component vector 281 is determined by taking the difference between the second transit time differential vector, $\Delta t_2$, and the second transit time differential vector primed, $\Delta t'_2$. A resultant automatically calibrated fluid velocity vector 282 is determined by combining the component vectors, 280 and 281.

Figure 3:
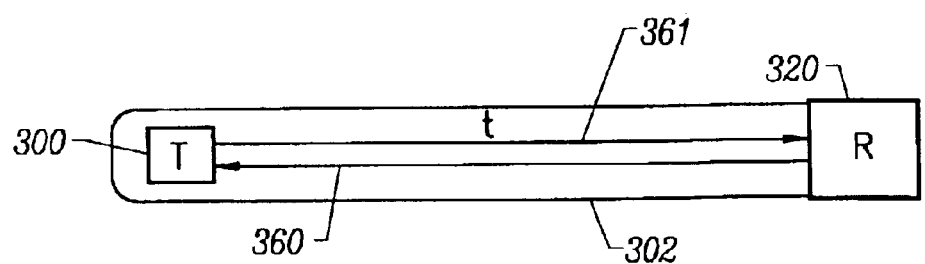
FIG. 3 is a diagram of the third preferred embodiment, according to the invention.

FIG. 3 is a diagram of a third exemplary embodiment of an apparatus for calculating density measurement in external pressure-temperature. A transmitter element 300, T, is adapted to transmit ultrasonic pulses and is placed in a ventilated tube 302. A receiver element 320 is adapted to receive ultrasonic pulses. The tubed transmitter 300 is positioned a short distance the receiver 320. An ultrasonic pulse is transmitted from the tubed transmitter 300 to the receiver 320 and a transit time 361 for the pulse to reach the receiver 320 is calculated. A transit time differential measurement by taking a difference between the calculated transit time 361 and a predetermined transit time 360 of a generic ultrasonic pulse transmitted from the receiver 320 to the first transmitter 300 in standard atmospheric pressure. A density measurement is determined from the transit time differential measurement.

It should be appreciated that the first two embodiments work particularly well when the fluid whose speed is calculated is wind. The third embodiment works particularly well for calculating density altitude. It should be noted that all three exemplary embodiments are small, and therefore lightweight and relatively inexpensive. For example, a preferred distance between any transmitter and the receiver is approximately two feet. It should be noted that all three exemplary embodiments are adaptable to be portable. For example, the open transmitters and tubed transmitters can be coupled to foldable lightweight legs that fold open and closed for transporting by a person. It should be noted that in the open configuration, the receiver is sufficiently sensitive to receive the ultrasonic pulses. It should be noted that a preferred material for the ventilated tube is a lightweight plastic protective material. It should be noted that in all three exemplary embodiments, the measurements taken are digital, as opposed to analog, and are therefore more accurate. It should be noted that in all three exemplary embodiments, there are no moving parts to make the invention, for example, cumbersome, and to be distracting to a user.

The foregoing merely illustrates the principles of this invention, and various modifications can be made by persons of ordinary skill in the art without departing from the scope and spirit of this invention.

We claim:

1. A process for calculating an automatically calibrated gas velocity vector in external pressure-temperature, the process comprising:

providing first and second transmitters adapted to transmit ultrasonic pulses, wherein the first transmitter is in an open configuration and the second transmitter is in a first ventilated tube, such chat the second transmitter is positioned along a first axis;

providing third and fourth transmitters adapted to transmit ultrasonic pulses, wherein the third transmitter is in an open configuration and the fourth transmitter is in a second ventilated tube, such that the fourth transmitter is positioned along a second axis, the second axis perpendicular to the first axis;

providing a receiver adapted to receive ultrasonic pulses from the transmitters, whereby the first and second transmitters are each positioned a first distance from the receiver, the third and fourth transmitters are each positioned a second distance from the receiver and are each positioned at a 90 degree angle from the first and second transmitters;

transmitting a first ultrasonic pulse from the first transmitter to the receiver;

calculating a first transit time vector for the first pulse to reach the receiver;

transmitting a second ultrasonic pulse from the second transmitter to the receiver;

calculating a second transit time vector for the second pulse to reach the receiver;

transmitting a third ultrasonic pulse from the third transmitter to the receiver;

calculating a third transit time vector for the third pulse to reach the receiver;

transmitting a fourth ultrasonic pulse from the fourth transmitter to the receiver;

calculating a fourth transit time vector for the fourth pulse to reach the receiver;

calculating a first transit time differential vector by taking a first difference between the calculated first transit time vector and a first predetermined time transit vector;

calculating a second transit time differential vector by taking a second difference between the calculated second transit time vector and a second predetermined time transit vector;

calculating a third transit time differential vector by taking a third difference between the calculated third transit time vector and a third predetermined time transit vector;

calculating a fourth transit time differential vector by taking a fourth difference between the calculated fourth transit time vector and a fourth predetermined time transit vector;

calculating a first automatically calibrated gas velocity component vector by taking a first differential difference between the calculated first and second transit time differential vectors;

calculating a second automatically calibrated gas velocity component vector by taking a second differential difference between the calculated third and fourth transit time differential vectors; and determining the automatically calibrated gas velocity vector by combining the first automatically calibrated gas velocity component vector and the second automatically calibrated gas velocity component vector.

2. The process of claim 1, wherein a gas whose automatically calibrated gas velocity vector is being calculated is wind.

3. The process of claim 1, wherein the first distance is substantially two feet and the second distance is substantially two feet.

4. The process of claim 1, wherein the transmitters and the receiver are adapted to be portable.

5. The process of claim 1, wherein the receiver is sufficiently sensitive to receive the pulses in the open configuration.

6. The process of claim 1, wherein the transmitters are each ultrasonic piezoelectric transducers.

7. The process of claim 1, wherein the calculations are digital.

8. The process of claim 1, wherein the transmitters and the receiver contain no moving parts.

9. The process of claim 1, wherein the first and second ventilated tubes comprise a lightweight plastic protective material.

10. An apparatus for calculating an automatically calibrated gas velocity vector in external pressure-temperature, the apparatus comprising:

first and second transmitters adapted to transmit ultrasonic pulses, wherein the first transmitter is in an open configuration and the second transmitter is in a first ventilated tube, such that the second transmitter is positioned along a first axis;

third and fourth transmitters adapted to transmit ultrasonic pulses, wherein the third transmitter is in an open configuration and the fourth transmitter is in a second ventilated tube, such, that the fourth transmitter is positioned along a second axis, the second axis perpendicular to the first axis;

a receiver adapted to receive ultrasonic pulses from the transmitters, whereby the first and second transmitters are each positioned a first distance from the receiver, the third and fourth transmitters are each positioned a second distance from the receiver and are each positioned at a 90 degree angle from the first and second transmitters;

means for transmitting a first ultrasonic pulse from the first transmitter to the receiver;

means for calculating a first transit time vector for the first pulse to reach the receiver;

means for transmitting a second ultrasonic pulse from the second transmitter to the receiver;

means for calculating a second transit time vector for the second pulse to reach the receiver;

means for transmitting a third ultrasonic pulse from the third transmitter to the receiver;

means for calculating a third transit time vector for the third pulse to reach the receiver;

means for transmitting a fourth ultrasonic pulse from the fourth transmitter to the receiver;

means for calculating a fourth transit time vector for the fourth pulse to reach the receiver;

means for calculating a first transit time differential vector by taking a first difference between the calculated first transit time vector and a first predetermined time transit vector;

means for calculating a second transit time differential vector by taking a second difference between the calculated second transit time vector and a second predetermined time transit vector;

means for calculating a third transit time differential vector by taking a third difference between the calculated third transit time vector and a third predetermined time transit vector;

means for calculating a fourth transit time differential vector by taking a fourth difference between the calculated fourth transit time vector and a fourth predetermined time transit vector;

means for calculating a first automatically calibrated gas velocity component vector by taking a first differential difference between the calculated first and second transit time differential vectors;

means for calculating a second automatically calibrated gas velocity component vector by taking a second differential difference between the calculated third and fourth transit time differential vectors; and means for determining the automatically calibrated gas velocity vector by combining the first automatically calibrated gas velocity component vector and the second automatically calibrated gas velocity component vector.

11. The apparatus of claim 10, wherein a gas whose automatically calibrated gas velocity vector is being calculated comprises wind.

12. The apparatus of claim 10, wherein the first distance is substantially two feet and the second distance is substantially two feet.

13. The apparatus of claim 10, wherein the transmitters and the receiver are adapted to be portable.

14. The apparatus of claim 10, wherein the receiver is sufficiently sensitive to receive the pulses in the open configuration.

15. The apparatus of claim 10, wherein the transmitters are each ultrasonic piezoelectric transducers.

16. The apparatus of claim 10, wherein the calculations are digital.

17. The apparatus of claim 10, wherein the apparatus contains no moving parts.

18. The apparatus of claim 10, wherein the first and second ventilated tubes comprise a lightweight plastic protective material.

* * * * *

UNITED STATES PATENT AND TRADEMARK OFFICE
CERTIFICATE OF CORRECTION

PATENT NO. : 6,786,102 B2
DATED : September 7, 2004
INVENTOR(S) : Wood et al.

It is certified that error appears in the above-identified patent and that said Letters Patent is hereby corrected as shown below:

Column 3,
Line 26, kindly change "distance of" to -- distance 40 of --.

Column 5,
Line 42, kindly change "chat" to -- that --.

Signed and Sealed this

Fourteenth Day of December, 2004

JON W. DUDAS
*Director of the United States Patent and Trademark Office*